(12) United States Patent
Wagoner

(10) Patent No.: US 7,625,575 B2
(45) Date of Patent: *Dec. 1, 2009

(54) DERMATOLOGICAL COMPOSITION

(75) Inventor: Bruce Kevin Wagoner, Charlotte, NC (US)

(73) Assignee: Harmony Labs, Inc., Landis, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/857,958

(22) Filed: Sep. 19, 2007

(65) Prior Publication Data

US 2008/0138451 A1    Jun. 12, 2008

Related U.S. Application Data

(63) Continuation of application No. 10/723,777, filed on Nov. 26, 2003.

(51) Int. Cl.
*A61K 8/00* (2006.01)

(52) U.S. Cl. .................................................... 424/401

(58) Field of Classification Search ........................ None
See application file for complete search history.

(56) References Cited

U.S. PATENT DOCUMENTS

| | | | |
|---|---|---|---|
| 4,233,295 A | 11/1980 | Hill et al. | |
| 4,335,103 A | 6/1982 | Barker et al. | |
| 4,384,974 A | 5/1983 | Guthauser | |
| 4,401,650 A | 8/1983 | Salamone | |
| 4,454,118 A | 6/1984 | Johnson | |
| 4,578,267 A | 3/1986 | Salamone | |
| 4,659,495 A | 4/1987 | Figliola | |
| 5,529,987 A | 6/1996 | Gallina | |
| 5,569,651 A | 10/1996 | Garrison et al. | |
| 5,595,745 A | 1/1997 | Znaiden et al. | |
| 5,653,970 A * | 8/1997 | Vermeer ............... | 424/70.24 |
| 5,716,625 A | 2/1998 | Hahn et al. | |
| 5,804,203 A | 9/1998 | Hahn et al. | |
| 5,919,470 A | 7/1999 | Valdez et al. | |
| 5,997,889 A | 12/1999 | Durr et al. | |
| 6,121,317 A | 9/2000 | Wu et al. | |
| 6,139,850 A | 10/2000 | Hahn et al. | |
| 6,180,133 B1 | 1/2001 | Quan et al. | |
| 6,199,557 B1 | 3/2001 | Laughlin | |
| 6,251,374 B1 | 6/2001 | Laughlin | |
| 6,298,862 B1 | 10/2001 | Laughlin | |
| 6,305,384 B2 | 10/2001 | Laughlin | |
| 6,380,236 B2 | 4/2002 | Glassman | |
| 6,416,747 B1 | 7/2002 | Laughlin | |
| 6,429,231 B1 | 8/2002 | Bhagwat et al. | |
| 6,431,180 B2 | 8/2002 | Laughlin | |
| 6,439,243 B2 | 8/2002 | Laughlin | |
| 6,440,437 B1 | 8/2002 | Krzysik et al. | |
| 6,446,635 B2 | 9/2002 | Laughlin | |
| 6,468,508 B1 | 10/2002 | Laughlin | |
| 6,469,227 B1 | 10/2002 | Cooke et al. | |
| 6,474,343 B2 | 11/2002 | Laughlin | |
| 6,485,733 B1 | 11/2002 | Huard et al. | |
| 6,495,602 B1 | 12/2002 | Bhagwat et al. | |
| 6,517,848 B1 | 2/2003 | Huard et al. | |
| 6,521,241 B1 | 2/2003 | Minerath, III et al. | |
| 6,551,607 B1 | 4/2003 | Minerath, III et al. | |
| 6,573,301 B1 | 6/2003 | Glassman et al. | |
| 6,673,842 B2 | 1/2004 | Bhagwat et al. | |
| 2001/0003283 A1 | 6/2001 | Laughlin | |
| 2001/0029961 A1 | 10/2001 | Laughlin | |
| 2002/0000236 A1 | 1/2002 | Laughlin | |
| 2002/0000237 A1 | 1/2002 | Laughlin | |
| 2002/0005208 A1 | 1/2002 | Laughlin | |
| 2002/0040721 A1 | 4/2002 | Laughlin | |
| 2002/0088475 A1 | 7/2002 | Laughlin | |
| 2002/0195119 A1 | 12/2002 | Laughlin | |
| 2003/0000539 A1 | 1/2003 | Laughlin | |
| 2003/0003124 A1 | 1/2003 | Laughlin | |
| 2003/0019504 A1 | 1/2003 | Laughlin | |
| 2003/0094510 A1 | 5/2003 | Laughlin | |
| 2003/0124202 A1 | 7/2003 | Hahn et al. | |
| 2003/0212127 A1 | 11/2003 | Glassman et al. | |
| 2005/0048105 A1 | 3/2005 | McNulty et al. | |
| 2005/0112153 A1 | 5/2005 | Wagoner | |
| 2008/0138451 A1 | 6/2008 | Wagoner | |

OTHER PUBLICATIONS

Brasher, B., "Comman scents get you a head", "Times Union (found on-line at http://proquest.umi.com)", Sep. 20, 2001, pp. C-6, Published in: Albany, NY.

Flick, Ernest W., "Cosmetic and Toiletry Formulations, 2nd Ed., vol. 1", 1989, pp. 157, 313, Publisher: Noyes Publications, Published in: Park Ridge, NJ.

Flick, Ernest W., "Cosmetic and Toiletry Formulations, 2nd Ed., vol. 8", 2001, pp. 157, 313, Publisher: Noyes Publications, William Andrew Publishing, LLC, Published in: Norwich, NY.

Nagel, J.E., et al., "Paraben allergy", "JAMA", Apr. 11, 1977, pp. 1594-1595, vol. 237, No. 15.

Ortega-Garcia, Jesus, et al., "Refining of high oleic safflower oil: Effect on the sterols and tocopherols content", "Eur. Food Res. Tech.", Oct. 2006, pp. 775-779, vol. 223, No. 6.

* cited by examiner

*Primary Examiner*—Patricia Leith
(74) *Attorney, Agent, or Firm*—Steven J. Hultquist; Intellectual Property/Technology Law

(57) ABSTRACT

Dermatological compositions containing a humectant, e.g., at least one of urea, ammonium lactate, and glycerin, and an emollient, e.g., at least one of Shea or cocoa butter, glycine soja sterol and hybrid sunflower oil. The compositions of the invention may be utilized for treatment or amelioration of skin disorders or adverse physiological conditions, and such compositions may be employed as a base for cosmetic or pharmaceutical formulations for dermal administration.

11 Claims, No Drawings

DERMATOLOGICAL COMPOSITION

RELATED APPLICATION DATA

This application is a continuation of U.S. application Ser. No. 10/723,777, filed Nov. 26, 2003, and published on May 26, 2005 as U.S. Patent Application Publication No. US 2005/0112153 A1, the entire contents of which are incorporated by reference herein in their entirety.

FIELD OF THE INVENTION

The present invention relates to dermatological compositions useful as skin protectants, or alternatively as a base composition for use in cosmetic applications or in formulations for therapeutic application of pharmaceutical agents to the body via topical administration.

BACKGROUND OF THE INVENTION

In the field of dermatological compositions, a wide variety of formulations have been developed and commercialized. Such compositions include cosmetic formulations, skin care formulations and pharmaceutical formulations for topical administration of therapeutic agents to treat or prevent disease states and adverse physiological conditions.

Many such dermatological compositions have been formulated with preservatives such as parabens and other organic chemical compounds. Generally, it is advantageous to formulate dermatological compositions that are free of such preservatives or that otherwise minimize the amounts of such preservatives.

Concurrently, there is a progressive movement toward dermatological compositions having natural product ingredients, consistent with the goals of achieving enhanced biocompatibility, under the impetus of increasing environmental awareness, and avoiding adverse reactions that may occur in the use of dermatological compositions employing petroleum-based or other synthetic product ingredients.

Dermatological compositions frequently are formulated with humectant ingredients of widely varying types. Urea is a beneficial humectant, which has the additional advantages of keratolytic activity, and at higher concentrations the ability to solublize and denature proteins and the ability to exert mild antibacterial effects. Ammonium lactate is another humectant ingredient having desirable properties in dermatological compositions.

It would be a significant advance in the art to provide improved dermatological compositions that avoid high concentrations of traditional petroleum-derived formulation ingredients, that are free of conventional preservatives, that utilize natural product ingredients, and that are broadly useful for cosmetic, skin-care and pharmaceutical applications.

SUMMARY OF THE INVENTION

The present invention relates to dermatological compositions having utility for cosmetic, skin-care and/or pharmaceutical applications.

In one aspect, the present invention relates to a dermatological composition comprising a humectant including at least one of urea, ammonium lactate, and glycerin, and at least one emollient selected from the group consisting of *Butyrospernum Parkii* (Shea butter) fruit, glycine soja (soybean) sterol and *Helianthus Annuus* (hybrid sunflower) oil.

In another aspect, the invention relates to a dermatological composition including urea, and at least one of (i) Shea butter, (ii) glycine soja (soybean) sterol and (iii) *Helianthus Annuus* (hybrid sunflower) oil.

In another aspect, the invention relates to a dermatological composition containing ammonium lactate, in combination with at least one of Shea butter, glycine soja (soybean) sterol and *Helianthus Annuus* (hybrid sunflower) oil.

In a further aspect, the invention relates to dermatological compositions including from about 1 to about 50 percent by weight of urea, from about 2 to about 10 percent by weight Shea butter, from about 1 to about 4 percent by weight glycine soja (soybean) sterol, from about 2 to about 15 percent by weight *Helianthus Annuus* (hybrid sunflower) oil, with the balance being dermatologically acceptable excipients. In specific embodiments, such compositions may have a urea concentration of from about 5 to about 40 percent by weight, or alternatively a concentration of from about 20 to about 40 percent by weight, e.g., from about 21 percent by weight to about 40 percent by weight.

As used herein, references to compositional ingredients in percents by weight refers to weight percentages based on the total weight of the composition or formulation.

Compositions of the above-described types can also include from about 2 to about 10 percent by weight of emulsifier(s), such as glyceryl stearate and/or a dermatologically acceptable stearate derivative and/or stearic acid, or a dermatologically acceptable salt thereof. The compositions can also include from about 0.1 to about 1.5 percent by weight of a thickener, such as sodium polyacrylate or xanthan gum. The compositions can further include a pH adjusting agent such as triethanolamine, and/or a chelating agent such as EDTA or dermatologically acceptable salts thereof.

The various compositions of the invention may be in the form of lotions, creams, emulsions, suspensions, ointments, gels or other suitable forms capable of administration to the skin of a user. Accordingly, compositions in which water and/or water-miscible solvents are employed in varying amounts, are contemplated. Additionally, the compositions may be formulated with adjuvants, additional active ingredients and/or excipients, and/or other ingredients, to impart specific thixotropy, viscosity, flow, spreading, self-leveling, or other characteristics thereto, as necessary or desirable in specific formulations.

In another aspect, the invention relates to a composition including:
   (a) from about 1 to about 50 percent by weight urea;
   (b) from about 2 to about 10 percent by weight Shea butter;
   (c) from about 1 to about 4 percent by weight glycine soja (soybean) sterol;
   (d) from about 2 to about 15 percent by weight of *Helinthus annuus* (hybrid sunflower) oil;
   (e) from about 2 to about 10 percent by weight of an emulsifier;
   (f) from about 0.1 to about 1.5 percent by weight of a thickener; and
   (g) optionally, a pH adjusting agent, a chelating agent, an antioxidant, a preservative, water or a combination of water and a water-miscible solvent or other dermatologically acceptable components (e.g., other non-water soluble components), and/or mixtures thereof;

with the percentages by weight of all ingredients totaling to 100 weight percent.

In yet another aspect, the invention relates to a composition including:
   (a) from about 2 to about 15 percent ammonium lactate;
   (b) from about 2 and 10 percent by weight Shea butter;

(c) from about 1 and 4 percent by weight glycine soja (soybean) sterol;
(d) from about 2 to about 15 percent by weight of *Helinthus annuus* (hybrid sunflower) oil;
(e) from about 2 to about 10 percent by weight of an emulsifier;
(f) from about 0.1 to about 1.5 percent by weight of a thickener; and
(g) optionally, a pH adjusting agent, a chelating agent, a preservative, an antioxidant, a preservative, water or a combination of water and a water-miscible solvent or other dermatologically acceptable components (e.g., other non-water soluble components), and/or mixtures thereof;

with the percentages by weight of all ingredients totaling to 100 weight percent.

BHT is an example of a suitable antioxidant, EDTA (and salts thereof) is an example of a suitable chelating agent, sodium polyacrylate is an example of a suitable thickener, and triethanolamine is an example of a suitable pH adjusting agent.

A further aspect of the invention relates to a dermatological composition comprising a humectant including at least one of urea, ammonium lactate and glycerin, and an emollient including at least one of: (i) Shea butter, cocoa butter, or vegetable oil butter; (ii) plant-derived steroid alcohol and/or lecithin; and (iii) oxidation-stable natural oil.

In another aspect, the invention relates to a composition as variously described hereinabove, in combination with one or more additional components. Such additional components may include active and/or inactive (inert) ingredients. Additional components may include any of various botanical extracts, singly or in combination, that are included to impart specific beneficial attributes to the skin, tissue and/or nails. Examples of additional active components include enzymes such as papain to promote skin debriding, anti-microbials, anti-fungals (e.g., for treating fungal infections of the toenails or fingernails) and anti-inflammatory agents, particularly non-steroidal anti-inflammatory agents such as glucocorticosteroids.

A still further aspect of the invention relates to a method of treating skin, tissue and/or nails, involving applying to the skin, tissue and/or nails a composition as variously described hereinabove.

The compositions of the invention can be variously formulated and can be used, for example, to treat a wide variety of disorders of the skin, tissue and nails, such as psoriasis, ichthyosis, xerosis, keratosis, keratoderma, dermatitis, pruritis, eczema, calluses, and ingrown fingernails and/or toenails. The compositions can also be used to debride and/or soften the skin.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The dermatological compositions of the invention may be formulated in any suitable form for topical administration, including lotions, creams, emulsions, suspensions, ointments, gels, etc., depending on the specific combination and relative proportions of ingredients, including for example the amount of water and/or other solvents in the composition, and the amounts of any corresponding thickeners, fixatives, rheological agents, surface active agents, etc., as employed to provide a desired solid, semi-solid, liquid, or other form for application to the skin. Specific formulations can be made within the skill of the art, based on the disclosure herein, to yield appropriate compositions that are absorbable into the stratum corneum or otherwise administrable with effect to the skin.

The compositions of the invention may be formulated in variant manners, utilizing urea, ammonium lactate and/or glycerin as humectant components. As used herein, the term "ammonium lactate" is used broadly to refer to ammonium lactate per se, as well as to mixtures of ammonium lactate and lactic acid (and/or other alpha-hydroxy acids such as glycolic, malic, citric, etc.).

In urea-containing compositions of the invention, urea may be utilized in combination with at least one of Shea butter, glycine soja (soybean) sterol and *Helianthus Annuus* (hybrid sunflower) oil.

Set out in Table 1 below is a listing of potential ingredients, potential ranges and alternative species for selected components, in accordance with one aspect of the invention. In Table 1, the composition can further comprise water and/or other dermatologically compatible excipients in appropriate amounts for a given application.

TABLE 1

| Component | Concentration Range, Weight % | Alternative Components |
| --- | --- | --- |
| Urea | 1%-50% | ammonium lactate; glycerin; various combinations of these main and alternative components |
| Butylated Hydroxytoluene | 0.05%-0.5% | butylated hydroxyl anisol, ascorbyl palmitate, propyl gallate, alpha-tocopherol, citric acid, ascorbic acid, tocopherol acetate (tocopherols and derivatives thereof), grapeseed extract (*Vitis vinifera*), green tea extract (*Camellia sinensis*), retinyl palmitate, diacetyl methyl silicone |
| *Butyrospermum Parkii* (Shea Butter) Fruit | 0.5%-10% | cocoa butter, vegetable *jojoba* esters, *cera alba* (Beeswax), jojoba oil (*Simmondsia Chinensis*), castor oil, PEG 1500, |

TABLE 1-continued

| Component | Concentration Range, Weight % | Alternative Components |
|---|---|---|
| | | PEG 400, and modified vegetable oil "butters," mango butters |
| Disodium EDTA | 0.05%-0.3% | pentasodium DTPA, tetrasodium EDTA, furildioxime |
| Glyceryl Stearate | 2.0%-10.0% | polysorbate 60, glycol palmitate, glycol laurate, cetyl alcohol, soy lecithin, ceteareth-20 |
| *Glycine Soja* (Soybean) Sterol | 1.0%-4.0% | plant-derived steroid alcohols (e.g., sitosterol, stigmasterol, campesterol, brassicasterol, lanosterol, 7-dehydrocholesterol) and/or lecithin |
| *Helianthus Annuus* (Hybrid Sunflower) Oil | 2.0%-15% | oxidation-stable natural oils, e.g., oil obtained from plants such as rapeseed (*Brassica* spp.), soybean (*Glycine max*), oil palm (*Elaeis guineeis*), coconut (*Cocus nucifera*), castor (*Ricinus communis*), safflower (*Carthamus tinctorius*), mustard (*Brassica* spp. and *Sinapis alba*), coriander (*Coriandrum sativum*) linseed/flax (*Linum usitatissimum*), thale cress (*Arabidopsis thaliana*) and maize (*Zea mays*) |
| Sodium Polyacrylate | 0.1%-1.5% | other thickeners or thickening/emulsifying/ stabilizing additives, e.g., methyl cellulose, PEG-150 distearate, lecthin, cetearyl alcohol, carbomer, acrylic copolymers, polyacrylamides, beeswax, magnesium aluminum silicate, hydrogenated castor oil, xanthum gum, behenyl alcohol, stearyl alcohol, PEG 4000, PEG 6000, polyoxyethylene distearate, glyceryl polymethacrylate |
| Stearic Acid | 3.0%-8.0% | other fatty acid emulsifiers, e.g., lauric acid, myristic acid |
| Triethanolamine | 0.25%-2.5% | other pH adjusting agents, e.g., basic pH adjusting agents such as sodium hydroxide, ammonium hydroxide, potassium hydroxide, monethanolamine, diethanolamine, diisopropanolamine, aminomethylpropanol, tromethamine, tetrahydroxypropyl ethylenediamine |

Compositions in accordance with Table 1 can be variously formulated, wherein the weight percentages of all ingredients total to 100 weight percent.

The compositions of the invention can be formulated with pH adjusting agents to impart any suitable pH characteristic to the specific dermatological composition, e.g., a substantially neutral pH. In specific embodiments, it may be desirable to formulate the composition as having an initial pH in a range of from about 4 to about 10, or in a range of from about 7 to about 10, or in a range of from about 7.5 to about 9.0, depending on the specific utilization of the composition.

In other specific compositions, time-release pH adjustment agents may be employed, to counteract the tendency of urea to produce ammonia, resulting in progressively increasing pH of the composition, during extended storage or use of the composition.

Compositions of Table 1 may be formed with water or mixtures of water and water-miscible solvent(s). Examples of water-miscible solvents include alcohols and glycols. The relative proportions of water or water and water-miscible solvents(s) in specific compositions of the invention may be widely varied. For example, compositions may include cream formulations having a low relative amount of water, in comparison to lotions or emulsions having a higher relative proportion of water.

Concerning the reasons for the specific concentration ranges of ingredients set out in Table 1, such ranges have been determined to provide dermatological compositions of superior character, relative to compositions having ingredients outside of such concentration ranges. Nonetheless, it will be understood that compositions of the invention may be widely varied, to include relatively higher or lower concentrations than those set out in Table 1, or to include different numbers and types of ingredients therein, in specific embodiments.

In general, the amount of urea in urea-containing compositions of the invention should be at least 1% to provide a desired substantial humectant effect. Amounts of urea typically do not exceed above 50 weight percent, in order to provide optimal dermatological compatibility. In particular embodiments, the amount of urea may be preferably in a range of from about 5 to about 41 percent, more preferably in a range of from about 10 to about 40 percent, and most preferably in a range of from about 20 to about 40 percent.

The amounts of Shea butter, glycine soja sterol and hybrid sunflower oil are advantageously utilized in the amounts identified in Table 1, in order to provide a desired level of emolliency in the composition. The amounts of other components such as antioxidants, chelants, emulsifiers, thickeners and/or pH adjusting agents may be varied in respect of particular relative proportions that achieve the specific functional characteristics for which such ingredients are utilized in the composition.

Ammonium lactate-containing compositions of the invention may be formulated with ammonium lactate in amounts appropriate to the dermatological application of the composition, in combination with at least one of Shea butter, glycine soja sterol and hybrid sunflower oil. In specific embodiments, the ammonium lactate may be present in amounts of from about 1 to about 15 weight percent, more specifically from about 2 to about 12 weight percent, and most specifically from about 5 to about 12 weight percent. In a further specific embodiment, an ammonium lactate-containing composition may be formulated at 12% lactic acid content, and partially neutralized with ammonium hydroxide, e.g., at a concentration of 1.75% of formula weight, to obtain a specific desired pH.

Table 2 below sets out ingredients, concentrations and potential equivalents for illustrative ammonium lactate-containing compositions in specific embodiments of the invention.

Dermatological compositions of the invention may be utilized for treatment of a wide variety of dermal conditions and adverse physiological states manifesting dermally, including, without limitation, dry skin/xerosis, psoriasis, ichthyosis, keratosis, keratoderma, dermatitis, pruritis, eczema, callouses, and ingrown nails. Compositions of the invention are usefully employed as skin moisturizers, skin softening agents, skin debridement agents, etc., as well as base composition for cosmetic formulations, as well as base compositions for therapeutic, e.g., pharmacological, formulations. In cosmetic formulations, the compositions of the invention may be used with added ingredients that are solely cosmetic. Alternatively, the cosmetic formulation may include ingredients that are both cosmetically efficacious and therapeutically effective, e.g., so-called "cosmeceutical" ingredients.

In therapeutic formulations, the compositions of the invention may be utilized as base compositions for topical administration of therapeutic agents such as wound healing agents, anti-inflammatory agents, e.g., non-steroidal anti-inflammatory agents, glucocorticosteroids (e.g., hydrocortisone, triamcinolone, betamethasone, or their respective derivatives, or ibuproprofen, ketoprofen, methyl salicylate, etc.), anti-infective (antibiotic) agents (e.g., bacitracin, polymixin B, mupirocin, neomycin, and mixtures thereof), enzymes, anti-fungal agents, anti-viral agents, acne-combating agents, rosacea-combating agents, dermatitis-combating agents, topical immunomodulator agents, etc., as well as any other agents that are beneficially applied to the skin to treat or ameliorate symptoms of physiological disorders and disease states susceptible to such treatment or amelioration.

Set out below in Table 3 is a tabulation of therapeutic agents by category and specific examples, and associated indications (disease states or adverse physiological conditions or symptoms) for which dermatological compositions of the invention may be utilized in therapeutic formulations. In the use of such therapeutic agents, the composition of the invention as variously described hereinabove, comprising humectant, emollients and optional additional excipients, is utilized as a base to which the therapeutic agent is added in a therapeutically effective amount to yield a corresponding therapeutic composition for combating the appertaining disease state or adverse physiological condition constituting the specific indication.

TABLE 2

| Component | Concentration Range, Weight % | Alternative Components |
|---|---|---|
| Ammonium lactate/lactic acid | 1%-15% | other alpha-hydroxyl acids (e.g., glycolic, malic, citric, etc.) |
| Butylated Hydroxytoluene | 0.05%-0.5% | Other antioxidants, e.g., butylated hydroxyl anisol |
| *Butyrospermum Parkii* (Shea Butter) Fruit | 0.5%-10% | Cocoa butter, vegetable jojoba esters |
| Disodium EDTA | 0.05%-0.3% | Other chelants |
| Glyceryl Stearate | 2.0%-10.0% | Other emulsifiers, e.g., stearates |
| *Glycine Soja* (Soybean) Sterol | 1.0%-4.0% | Plant-derived steroid alcohols |
| *Helianthus Annuus* (Hybrid Sunflower) Oil | 2.0%-15% | Oxidation-stable natural oils |
| Sodium Polyacrylate | 0.1%-1.5% | Other thickeners or thickening/emulsifying/stabilizing additives, e.g., methyl cellulose |
| Stearic Acid | 3.0%-8.0% | Other fatty acid emulsifiers |
| Triethanolamine | 0.25%-2.5% | Other pH adjusting agents, e.g., basic pH adjusting agents such as sodium hydroxide, ammonium hydroxide, etc. |

The reasons for the specific ranges of ingredients that are identified in Table 2 are analogous to those discussed hereinabove in connection with Table 1 urea-containing compositions of the invention.

TABLE 3

| Active Ingredient Category | Active Ingredient Examples | Possible Indications for Active Ingredient |
| --- | --- | --- |
| Wound Healing | papain, trypsin, allantoin, chymotrypsin, streptokinase, streptodornase, ficin, pepsin, carboxypeptidase, aminopeptidase, chymopapain, bromelin | skin debridement agent, accelerator for wound healing |
| Anti-Inflammatory | hydrocortisone, triamcinolone, betametamethasone, ibupropfen, ketoprofen, methyl salicylate, dexamethasone, prednisolone, cortisone, prednisone, beclomethasone, betamethasone, flunisolide, fluocinolone acetonide, fluocinonide, indomethacin, diclofenac sodium, mefenamic acid, azulene, phenacetin, isopropylantipyrine, acetaminophen, bendzac, phenylbutazone, flufenamic acid, sodium salicylate, salicylamide, sasapyrine, etodolac | reducer of redness, itching and swelling, contact dermititis |
| Anti-Infectives | bacitracin, polymixin B, mupirocin, neomycin, tetracyclines (chlortetracycline hydrochloride, oxytetracycline hydrochloride and tetracycline hydrochoride), clindamycin, gentamicin sulfate, benzalkonium chloride, benzethonium chloride, hexylresorcinol, methylbenzethonium chloride, phenol | topical bacterial infections, impetigo, folliculitis, carbuncles |
| Anti-Fungals | miconazole, econazole, tolnaftate, ketoconazole, undecylenic acid, amphotericin B, carbol-fuchsin, ciclopirox, clotrimzole, haloprogin, mafenide, naftifine, nystatin, oxiconazole, silver, sulfadiazine, sulconazole, terbinafine, tioconazole, undecylenic acid | tinea pedis, tinea capitis, tinea cruris, tinea corporis, tinea versicolor, topical candidiasis |
| Anti-Acne | salicylic acid, benzoyl peroxide, resorcinol, sulfur, sodium sulfacetamide, retinoic acid, isotretinoin, erythromycin, zinc, retinol, citric acid, and alpha hydroxy acid | Acne, rosacea, seborheic dermatitis |
| Anti-Virals | acyclovir, docosanol, pencyclovir, cidofovir, desciclovir, famciclovir, ganciclovir, lobucavir, PMEA, valacyclovir, 2242, PAA, PFA, H2G, sorivudine, trifluridin, tromantadine, adenine, arabinoside, arabinosyladenine-monophosphate, lobucavir | Topical treatment of HSV-1, HSV-2, Vericella-Zoster |
| Topical Immunomodulators | pimecrolimus, tacrolimus, muramyl dipeptide, cyclosporins, interferons (including alpha, beta, and gamma interferons), interleukin-2, cytokines, tumor necrosis factor, pentostatin, thymopentin, transforming factor $\beta_2$, erythropoetin | atopic dermatitis |

In like manner, the compositions of the invention may be employed in cosmetic applications, by addition thereto of a cosmetically effective amount of a cosmetic agent, e.g., in the form of a pigment, powder, microencapsulated particulate, etc., together with adjuvants, excipients, and the like that are appropriate to such application of the composition.

More generally, dermatological compositions of the invention may be formulated with a wide variety of excipients, including emulsifiers and thickeners, as are conventionally employed in skin care products and in specific forms (creams, lotions, emulsions, suspensions, ointments, gels, etc.).

Examples of dermatologically acceptable excipients include, without limitation, emulsifiers, thickeners, pH adjusting agents, chelating agents, and preservatives.

Emulsifiers include, for example, $C_{16-18}$ straight or branched chain fatty alcohols or fatty acids or mixtures thereof, such as cetyl alcohol, stearyl alcohol, stearic acid, palmitic acid, and mixtures thereof. Glyceryl stearate is another suitable emulsifier, which is also available commercially as a self-emulsifying grade of glycerol stearate (i.e., glycerol stearate SE, which typically contains some sodium and/or potassium stearate).

Thickeners include compounds like sodium polyacrylate and xanthan gum. Xanthan gum is a high molecular weight heteropolysaccharide gum produced by pure-culture fermentation of a carbohydrate with *Xanthomonas campestris*. Another suitable thickener is a mixture of a carbomer and triethanolamine. The carbomers come in various molecular weights and identified by numbers. These are commercially known as Carbopols. Carbopols are homopolymers of acrylic acid crosslinked with an allyl ether of pentaerythritol, an allyl ether of sucrose or an allyl ether of propylene. Carbomers can be used as thickeners, and also help to suspend and stabilize the emulsion. Illustrative Carbopols include Carbopol 940, carbomer 910, 2984, 5984, 954, 980, 981, 941 and 934, Carbopol ETD 2001, 2020, and 2050 and Ultrez 20. The mixture is combined together and added to the composition in an amount totaling anywhere from about 0.05 to about 30 wt-%.

Still other thickeners that may be usefully employed in particular compositions of the invention include methyl cellulose, polyethylene glycol species such as PEG-150, PEG 4000 and PEG 6000, distearate, lecithin, cetearyl alcohol, acrylic copolymers, polyacrylamides, beeswax, magnesium aluminum silicate, hydrogenated castor oil, behenyl alcohol, stearyl alcohol, polyoxyethylene distearate, glyceryl polymethacrylate, and the like.

Butylated hydroxy toluene (BHT) and analogs thereof, and various other components may be employed as stabilizers for the composition. Various pH-adjusting agents may be employed in compositions of the invention, including, by way of example, hydroxide salts (i.e., calcium hydroxide, sodium hydroxide, potassium hydroxide) and amines, such as triethanolamine. Triethanolamine (also known as Trolamine) is a preferred pH-adjusting agent.

Dermatological compositions of the present invention may be readily formulated in any suitable manner. In one embodiment, the composition is prepared by mixing the humectant, such as urea, ammonium lactate and/or glycerin, with an appropriate amount of water or water-miscible solvent mixture for the composition. The mixing operation may be carried out at temperature in a range of from ambient (room temperature) to elevated temperature of 85-95° C. The mixing may be carried out utilizing a Cowles mixer or other suitable mixing device, e.g., a sonicator, paddle mixer, helical static mixer apparatus, or the like. The water preferably is pre-purified to appropriate purity for the composition. Mixing is carried out for sufficient duration to fully solublize the humectant component in the aqueous medium. Concurrently, the remaining ingredients are separately mixed by addition mixing of such components, and such mixing may be carried out at suitable temperature, e.g., in a range of from about ambient (room temperature) to 85-95° C., for sufficient duration to homogenize the mixture of ingredients. The respective volumes of ingredients then are consolidated under mixing conditions at suitable temperature, e.g., in a range of from about ambient (room temperature) to about 75-80° C., followed by cooling (if the composition is at elevated initial temperature) to ambient temperature followed by packaging of the product into suitable containers for storage, transport and ultimate use.

Alternatively, all of the other ingredients of the composition may be added simultaneously or sequential or in other order to water or to a water and water-miscible solvent mixture, under agitation or other mixing conditions, to homogenize the material and produce a composition of the desired consistency in the specific product form (e.g., lotion, cream, gel, suspension, emulsion, etc.).

The features and advantages of the invention are more fully apparent from the following non-limiting examples, wherein all parts and percentages are by weight, unless otherwise expressly stated.

EXAMPLE 1

A dermatological lotion composition in accordance with the invention was formulated, including the following ingredients and concentrations, as identified in Table 4 below.

TABLE 4

| Ingredient | Percentage by Weight |
| --- | --- |
| Urea | 40 |
| Water | 39.10 |
| Disodium EDTA | 0.10 |
| Sodium polyacrylate | 0.60 |
| Stearic Acid | 4.0 |
| Glyceryl stearate | 3.0 |
| Soy Sterol | 2.0 |
| Sunflower oil | 8.0 |
| Shea Butter | 2.0 |
| Triethanolamine | 1.0 |
| BHT | 0.2 |

The composition was formulated by mixing of the respective ingredients to provide a homogeneous lotion. The lotion was tested by application to dermal surfaces and confirmed as being of appropriate character for skin moisturizer use.

EXAMPLE 2

A dermatological cream composition in accordance with the invention was formulated, including the following ingredients at the specified concentrations, as identified in Table 5 below.

TABLE 5

| Ingredient | Percentage by Weight |
| --- | --- |
| Urea | 40 |
| Water | 36.7 |
| Disodium EDTA | 0.10 |
| Sodium polyacrylate | 1.0 |
| Stearic Acid | 4.0 |
| Glyceryl stearate | 3.0 |
| Soy Sterol | 2.0 |
| Sunflower oil | 10.0 |
| Shea Butter | 2.0 |
| Triethanolamine | 1.0 |
| BHT | 0.2 |

The cream was formulated by mixing of the respective ingredients to provide a semi-solid cream. The cream was tested by application to dermal surfaces and confirmed as being of appropriate character for skin moisturizer use.

Although the invention has been described herein with respect to specific aspects, features and embodiments, it will be recognized that the invention is susceptible to application with other variations, modifications and alternative embodiments. Accordingly, the invention is intended to be broadly construed and interpreted, as encompassing all such variations, modifications and alternative embodiments within the spirit and scope of the invention as hereafter claimed.

What is claimed is:

1. A dermatological composition, consisting of water and the following components in the following respective concentration ranges:

| Component | Concentration Range, Weight % |
| --- | --- |
| Urea | 1%-50% |
| Butylated Hydroxytoluene | 0.05%-0.5% |
| *Butyrospermum Parkii* (Shea Butter) Fruit | 0.5%-10% |
| Disodium EDTA | 0.05%-0.3% |
| Glyceryl Stearate | 2.0%-10.0% |
| *Glycine Soja* (Soybean) Sterol | 1.0%-4.0% |
| *Helianthus Annuus* (Hybrid Sunflower) Oil | 2.0%-15% |
| Sodium Polyacrylate | 0.1%-1.5% |
| Stearic Acid | 3.0%-8.0% |
| Triethanolamine | 0.25%-2.5% | wherein weight % is based on the total weight of the composition and the weight percentages of all components in the composition totals 100%.

2. A dermatological composition according to claim 1, wherein the concentration of urea is in a range of from 21 to 40 weight %.

3. A dermatological composition according to claim 1, wherein the composition consists of water and the following components in the following respective concentrations:

| Component | Weight % |
| --- | --- |
| Urea | 40.0% |
| Butylated Hydroxytoluene | 0.2% |
| *Butyrospermum Parkii* (Shea Butter) Fruit | 2.0% |
| Disodium EDTA | 0.1% |
| Glyceryl Stearate | 3.0% |
| *Glycine Soja* (Soybean) Sterol | 2.0% |
| *Helianthus Annuus* (Hybrid Sunflower) Oil | 8.0% |
| Sodium Polyacrylate | 0.6% |
| Stearic Acid | 4.0% |
| Triethanolamine | 1.0% |

4. The composition of claim 3, in the form of a suspension.

5. A dermatological composition according to claim 1, wherein the composition consists of water and the following components in the following respective concentrations:

| Component | Weight % |
| --- | --- |
| Urea | 40.0% |
| Butylated Hydroxytoluene | 0.2% |
| *Butyrospermum Parkii* (Shea Butter) Fruit | 2.0% |
| Disodium EDTA | 0.1% |
| Glyceryl Stearate | 3.0% |
| *Glycine Soja* (Soybean) Sterol | 2.0% |
| *Helianthus Annuus* (Hybrid Sunflower) Oil | 10.0% |
| Sodium Polyacrylate | 1.0% |
| Stearic Acid | 4.0% |
| Triethanolamine | 1.0% |

6. The composition of claim 5, in the form of an emulsion.

7. A dermatological composition consisting of water and the following components in the following respective concentration ranges:

| Component | Concentration Range, Weight % |
| --- | --- |
| Urea, glycerin | 1%-50% |
| Butylated Hydroxytoluene | 0.05%-0.5% |
| *Butyrospermum Parkii* (Shea Butter) Fruit, wax | 0.5%-10% |
| Disodium EDTA | 0.05%-0.3% |
| *Helianthus Annuus* (Hybrid Sunflower) Oil | 2.0%-15% |
| Sodium Polyacrylate, polyacrylamides, wax, paraffins | 0.1%-1.5% |
| Lauric Acid | 3.0%-8.0% | and further comprising water, wherein weight % is based on the total weight of the composition and the weight percentages of all components in the composition totals 100%.

8. The dermatological composition of claim 7, wherein the concentration of urea is 40%.

9. A method for treating a skin condition selected from the group consisting of psoriasis, xerosis, ichthyosis, keratosis, keratoderma, dermatitis, pruritus, eczema and calluses comprising topically applying an effective amount of the composition of claim 1 to a subject having said skin condition.

10. A method for softening skin tissue or softening nails comprising topically applying an effective amount of the composition of claim 1 to skin or nails of a subject in need thereof.

11. A lotion, cream, ointment, emulsion, suspension or gel consisting essentially of the dermatological composition of any one of claims 1, 3, 5, or 7.

* * * * *